United States Patent
Ohtsuka (10) Patent No.: US 7,871,379 B2
(45) Date of Patent: Jan. 18, 2011

(54) ULTRASONIC DIAGNOSTIC APPARATUS AND METHOD OF ULTRASONIC MEASUREMENT

(75) Inventor: Noriaki Ohtsuka, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 23 days.

(21) Appl. No.: 11/454,927

(22) Filed: Jun. 19, 2006

(65) Prior Publication Data

US 2007/0038086 A1 Feb. 15, 2007

(30) Foreign Application Priority Data

Jun. 20, 2005 (JP) ............................. 2005-179171
May 12, 2006 (JP) ............................. 2006-133819

(51) Int. Cl.
*A61B 8/00* (2006.01)

(52) U.S. Cl. ...................................... 600/443; 715/781

(58) Field of Classification Search ................. 600/446; 715/781, 782
See application file for complete search history.

(56) References Cited

U.S. PATENT DOCUMENTS

| | | | |
|---|---|---|---|
| 4,584,880 A | | 4/1986 | Matzuk |
| 5,947,904 A * | | 9/1999 | Hossack et al. ............. 600/458 |
| 5,954,650 A * | | 9/1999 | Saito et al. .................. 600/425 |
| 6,083,168 A * | | 7/2000 | Hossack et al. ............. 600/443 |
| 6,126,600 A * | | 10/2000 | Oxaal et al. ................. 600/439 |
| 6,203,498 B1 * | | 3/2001 | Bunce et al. ................ 600/446 |
| 6,436,049 B1 * | | 8/2002 | Kamiyama et al. ......... 600/458 |
| 6,468,212 B1 * | | 10/2002 | Scott et al. .................. 600/437 |
| RE38,209 E * | | 8/2003 | Yamazaki et al. |
| 6,849,048 B2 * | | 2/2005 | Omiya ........................ 600/443 |
| 6,884,216 B2 | | 4/2005 | Abe et al. |
| 6,984,210 B2 * | | 1/2006 | Chambers et al. ........... 600/443 |
| 7,285,092 B2 * | | 10/2007 | Duric et al. ................. 600/443 |
| 2002/0173721 A1 * | | 11/2002 | Grunwald et al. ........... 600/437 |
| 2003/0109779 A1 * | | 6/2003 | Ohishi et al. ................ 600/407 |
| 2003/0163044 A1 * | | 8/2003 | Heimdal et al. ............. 600/437 |
| 2003/0176787 A1 * | | 9/2003 | Gilbert et al. ............... 600/437 |
| 2003/0199766 A1 * | | 10/2003 | Kato ........................... 600/443 |
| 2004/0015079 A1 * | | 1/2004 | Berger et al. ................ 600/437 |
| 2004/0087856 A1 * | | 5/2004 | Panda et al. ................. 600/443 |
| 2004/0111028 A1 * | | 6/2004 | Abe et al. .................... 600/437 |
| 2004/0116813 A1 * | | 6/2004 | Selzer et al. ................ 600/467 |

FOREIGN PATENT DOCUMENTS

CN 85 1 08130 A 5/1987
JP 2004-73287 3/2004

* cited by examiner

*Primary Examiner*—Long V Le
*Assistant Examiner*—Saurel J Selkin
(74) *Attorney, Agent, or Firm*—Oblon, Spivak, McClelland, Maier & Neustadt, L.L.P.

(57) ABSTRACT

A display mode switching unit is provided to input a display mode switching signal for selecting a dynamic image display mode and a freeze image display mode. A display format setting unit is provided to set a first display format for displaying image data and time-series data by Left/Right. The display format setting unit sets a second display format for displaying the image data and time-series data by Up/Down or for displaying the time-series data. A display data generation unit generates display data including the first display format when the dynamic image display mode is selected. The display data generation unit generates display data including the second display format when the freeze image display mode is selected.

18 Claims, 9 Drawing Sheets

ULTRASONIC DIAGNOSTIC APPARATUS AND METHOD OF ULTRASONIC MEASUREMENT

CROSS-REFERENCE TO RELATED APPLICATION

This application is based upon and claims the benefit of priority from the prior Japanese Patent Applications No. 2005-179171 filed on Jun. 20, 2005 and No. 2006-133819 filed on May 12, 2006, the entire contents of which are incorporated herein by reference.

FIELD OF THE INVENTION

The present invention relates to an ultrasonic diagnostic apparatus and, more particularly, to an ultrasonic diagnostic apparatus and a method for performing various ultrasonic measurements by using time-series data.

DESCRIPTION OF THE BACKGROUND

An ultrasonic diagnostic apparatus is designed to emit ultrasonic pulses generated by ultrasonic transducers disposed in an ultrasonic probe into an object to be examined. The ultrasonic diagnostic apparatus receives reflected ultrasound or signals produced due to differences in acoustic impedance among the tissues of the object. The ultrasonic diagnostic apparatus displays image data on a monitor, which is generated based on received signals corresponding to the reflected ultrasound. This diagnostic method allows easy observation of real-time two-dimensional images by simple operation of only bringing the ultrasonic probe into contact with the body surface, and it is widely used for functional diagnosis or morphological diagnosis of various organs in a living body. Ultrasonic diagnostic method, which obtains information by using reflected ultrasound from tissue or blood cells in the living body, have rapidly progressed along with two great technical developments of an ultrasonic reflection method and an ultrasonic Doppler method. And B-mode images and color Doppler images obtained by these techniques have become indispensable to recent ultrasonic image diagnosis.

On the other hand, a Doppler spectrum method and an M-mode method are available as a method of obtaining information of blood flow and moving function of heart wall in the object to be examined with quantitatively and sufficient accuracy.

In this Doppler spectrum method, ultrasonic transmission/reception is performed with respect to the same region of the object at predetermined intervals, and Doppler signals are detected by performing quadrature phase detection for reflected ultrasound from moving reflectors such as blood cells. In the quadrature phase detection, a reference signal is used which has a frequency almost equal to the resonance frequency of the ultrasonic transducers. A Doppler signal from a desired area (hereinafter mentioned as the "region of interest (ROI)") is extracted from these Doppler signals by using a range gate, and Doppler spectrum data is generated by FFT (fast Fourier transform)-analyzing the extracted Doppler signal.

According to such a sequence, Doppler spectrum are continuously generated with respect to the Doppler signal obtained from the ROI in the object, and a plurality of Doppler spectrum data are sequentially arrayed to generate Doppler spectrum data. The Doppler spectrum data obtained by this ultrasonic Doppler method is generally displayed with a ordinate representing frequency, a abscissa representing time, and the power (intensity) of each frequency component being represented by a luminance (gray level). Various kinds of diagnosis parameters are measured on the basis of this Doppler spectrum data.

In the M-mode method, B-mode data are obtained by repeating ultrasound transmission to and ultrasound reception from a predetermined direction, and a plurality of B-mode data are sequentially arrayed to generate M-mode data. The M-mode data is displayed with an ordinate representing distance between the ultrasonic probe and reflectors, an abscissa representing time, and the reflective intensity of reflectors being represented by a luminance (gray level).

Usually, a position of the range gate which determines a collection position of Doppler spectrum data and a collection direction of M-mode data are set under B-mode image observation or colored Doppler image observation. A marker which shows the collection position and the collection direction are indicated on these images.

On the other hand, as a method of displaying Doppler spectrum data and M-mode data (hereinafter mentioned as the "time-series data") on the monitor, which has limited display width, a scroll method and a moving bar method are proposed. In the scroll method, time-series data are shifted in a direction of time-axis one by one, and in the moving bar method, a cursor perpendicular to the time-axis is moved in the direction of the time-axis, and time-series data is updated to the newest one at this cursor position.

A setup of the collection position of time-series data is performed under observation of B-mode image data or colored Doppler image data (hereinafter mentioned as the "image data") obtained in parallel with the time-series data, as described in Japanese Patent Publication (Kokai) No. 2004-73287, for example, and image data and time-series data are displayed simultaneously on the monitor.

According to a display method of image data and time-series data for setting the ROI described in this patent Publication, a display format (hereinafter mentioned as the "Left/Right display format") is used which displays image data and time-series data in a left/right direction and side by side. By applying this display format, display of comparatively large image data is possible and the ROI can be set up correctly.

However, when displaying time-series data obtained from a desired ROI as freeze data and measuring various diagnostic parameters using the time-series data are carried out, the time-series data generated based on the Left/Right display format can not show a direction of time-axis broadly, and the measurement of diagnostic parameter is difficult. For this reason, in the measurement of diagnostic parameters, for example, a display format (hereinafter mentioned as "Up/Down display format") which displays image data and time-series data in a vertical direction and side by side or a display format which displays only time-series data are used. By using these display formats, wide range time-series data can be displayed in the direction of the time-axis.

That is, when an operator measures diagnostic parameters using the time-series data which is displayed as freeze data, he needs to carry out a switching operation to a suitable display format. Especially, when a dynamic image display mode for setting the ROI and a freeze image display mode for measuring diagnostic parameters are repeated one after the other, manual change of the display format by the operator has become one of factors which reduce diagnostic efficiency remarkably.

SUMMARY OF THE INVENTION

It is an object of the present invention to provide an ultrasonic diagnostic apparatus and a method for performing ultrasonic measurements capable of improving diagnostic efficiency by changing a display format automatically according to the change of a display mode or a measurement mode, when various measurements are performed on the basis of the time-series data obtained by ultrasonic transmission/reception To achieve the object, a first aspect of the present invention may provide an ultrasonic diagnostic apparatus including an ultrasonic probe having ultrasonic transducers configured to transmit and receive ultrasound in a direction of an object to be examined, a transmission/reception unit configured to drive the ultrasonic transducers to transmit the ultrasound and receive reflected signals from the object, a data generation unit configured to generate ultrasonic data by processing the received reflected signals obtained by the transmission/reception unit, an image/time-series data generation unit configured to generate image data and time-series data by processing the ultrasonic data obtained by the data generation unit, a display mode switching unit configured to input a display mode switching signal for a dynamic image display mode and a freeze image display mode, a display format setting unit configured to set a display format of the image data and the time-series data in each of the dynamic image display mode and the freeze image display mode, a display data generation unit configured to generate display data including at least one of the image data and the time-series data based on the display format corresponding to the display mode switching signal and a display unit configured to display the display data.

A second aspect of the present invention may provide an ultrasonic diagnostic apparatus including an ultrasonic probe having ultrasonic transducers configured to transmit and receive ultrasound in a direction of an object to be examined, a transmission/reception unit configured to drive the ultrasonic transducers to transmit the ultrasound and receive reflected signals from the object, a data generation unit configured to generate ultrasonic data by processing the received reflected signals obtained by the transmission/reception unit, an image/time-series data generation unit configured to generate image data and time-series data by processing the ultrasonic data obtained by the data generation unit, a measurement item selection unit configured to select desired measurement item(s) from a plurality of measurement items for the time-series data, a display format setting unit configured to set a display format of the image data and the time-series data to the measurement item(s) selected by the measurement item selection unit, a display data generation unit configured to generate display data including at least one of the image data and the time-series data based on the display format corresponding to the display mode switching signal and a display unit configured to display the display data.

A third aspect of the present invention may provide a method of performing ultrasonic measurement including transmitting ultrasound to an object in a plurality of directions of an object, receiving signals from the object in response to the transmitted ultrasound, generating image data based on the received signals, setting a region of interest (ROI) on the image data generated based on a display format of a dynamic image display mode for acquiring time-series data, generating time-series data based on the received signals obtained by receiving ultrasound from an area of the object corresponding to the ROI, inputting a display mode switching signal, changing the display format from a dynamic image display mode to a freeze image display mode based on the display mode switching signal, displaying the display data including at least one of the image data and the time-series data based on the display format of the freeze image display mode and measuring diagnostic parameters based on the display data.

A fourth aspect of the present invention may provide a method of performing ultrasonic measurement including transmitting ultrasound to an object in a plurality of directions of an object, receiving signals from the object in response to the transmitted ultrasound, generating image data based on received signals, setting a region of interest (ROI) on the image data, generating time-series data based on the received signals obtained from an area of the object corresponding to the ROI, inputting a selection signal for selecting a measurement item, setting a display format of the image data and the time-series data based on the selection signal, generating the display data including at least one of the image data and the time-series data based on the display format and measuring the diagnostic parameter based on the display data.

In accordance with the aspects of the present invention, when various measurements are carried out based on time-series data obtained by transmitting ultrasound to and receiving reflected ultrasound from an object to be examined, a display format is automatically updated to suitable display format according to the display mode switching signal or measurement item selection information. Therefore, diagnostic efficiency is improved and the load on an operator can be reduced.

BRIEF DESCRIPTION OF THE DRAWINGS

Other object and features of the invention will become apparent to those skilled in the art as the disclosure is made in the following description of a preferred embodiment of the invention as illustrated in the accompanying sheet of drawings.

DETAILED DESCRIPTION OF THE INVENTION

In the embodiment described below, the display format of image data and time-series data in each of a dynamic image display mode and a freeze image display mode are selected beforehand. And image data (B-mode image data) and time-series data (Doppler spectrum data) obtained by ultrasonic transmission/reception to the object are displayed on a monitor in real time on the basis of a display format of the dynamic image display mode. Then, the image data and time-series data are displayed as freeze data on the basis of the display format of the freeze image display mode according to a display mode switching signal. And diagnostic parameters are measured by using the time-series data displayed on the monitor.

(Composition of Ultrasonic Diagnostic Apparatus)

Figure 1:
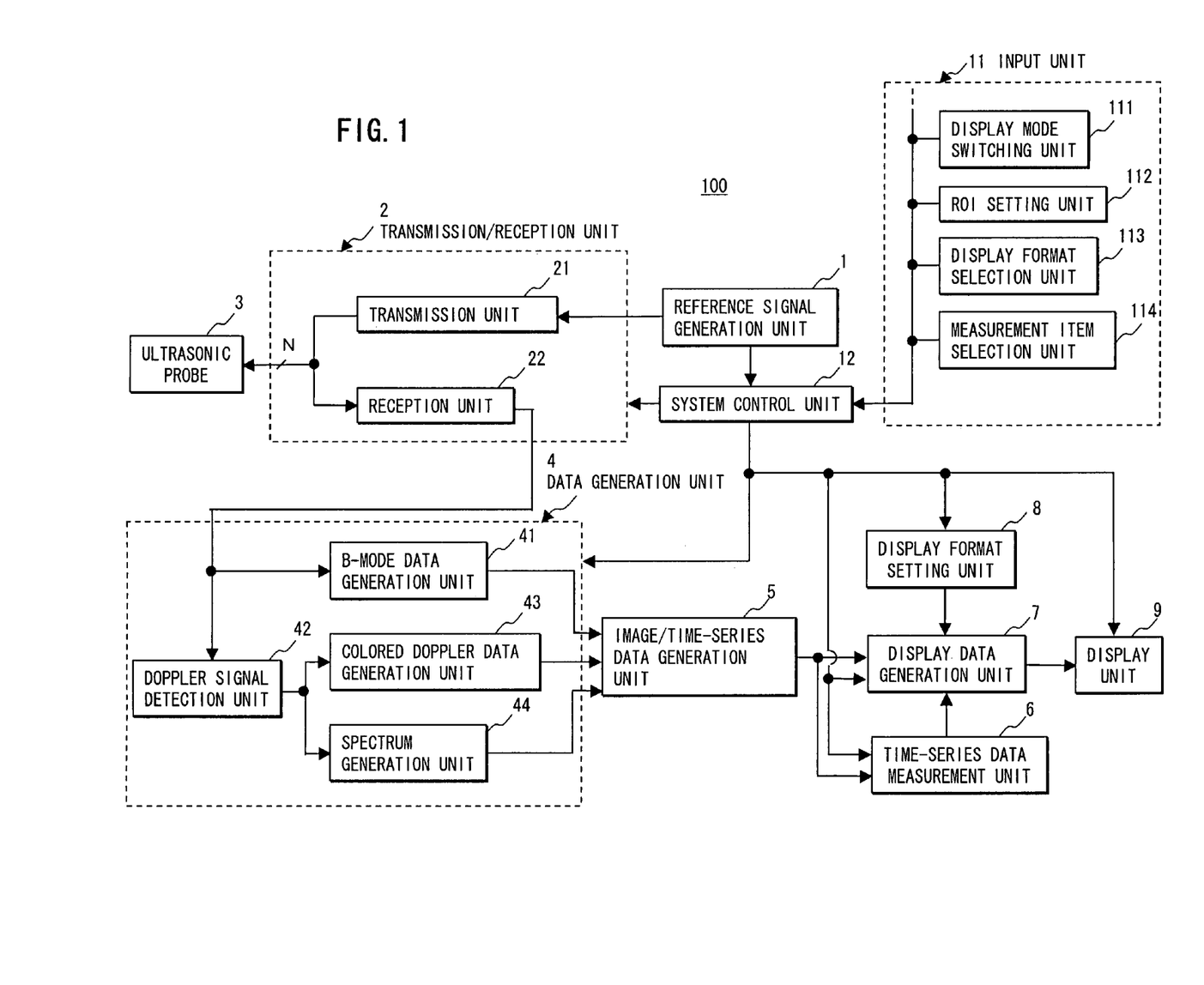
FIG. 1 is a block diagram showing the overall composition of an ultrasonic diagnostic apparatus according to an embodiment of the present invention.
Figure 2:
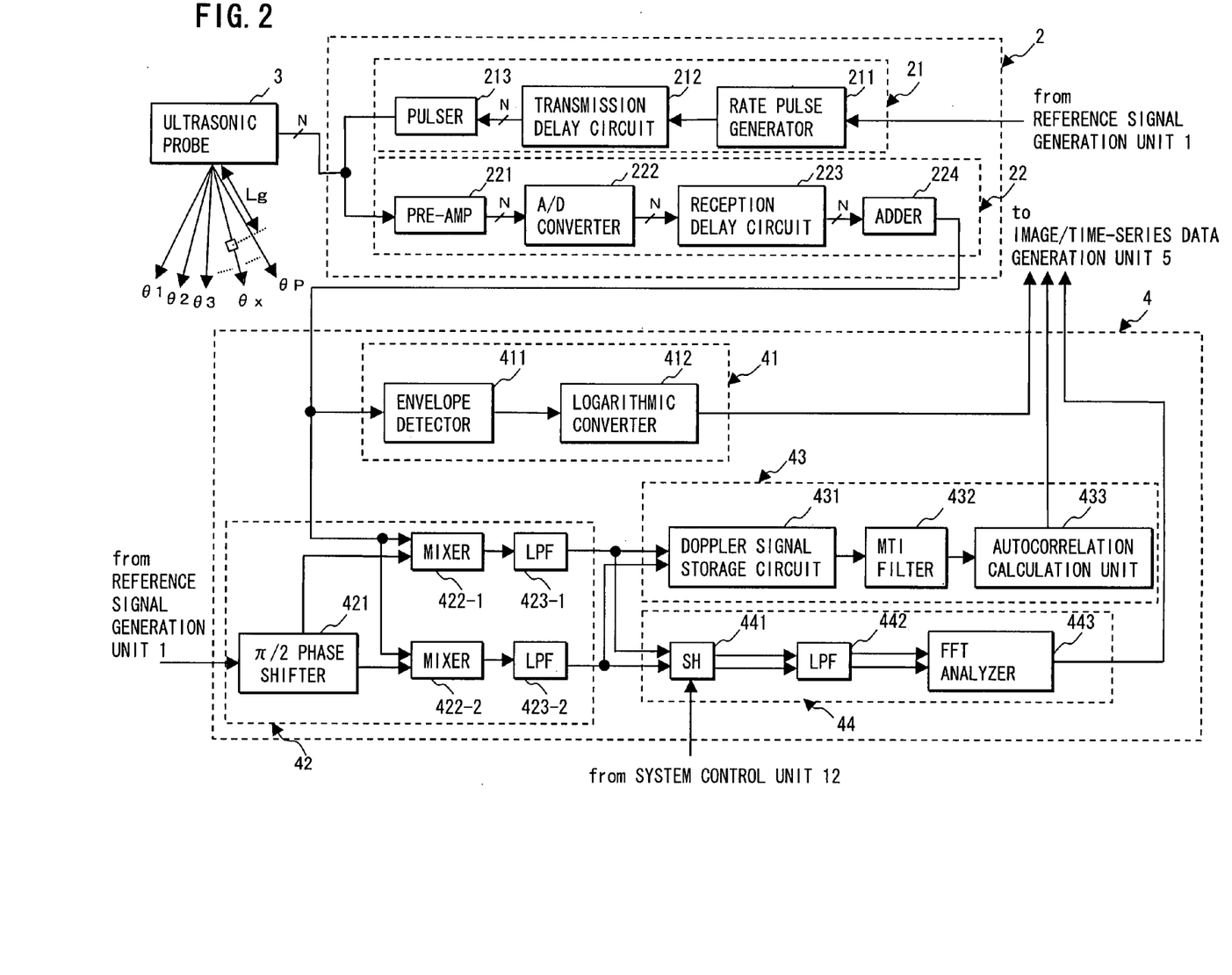
FIG. 2 is a block diagram showing the composition of a transmission/reception unit and a data generation unit in the embodiment shown in FIG. 1.
Figure 3:
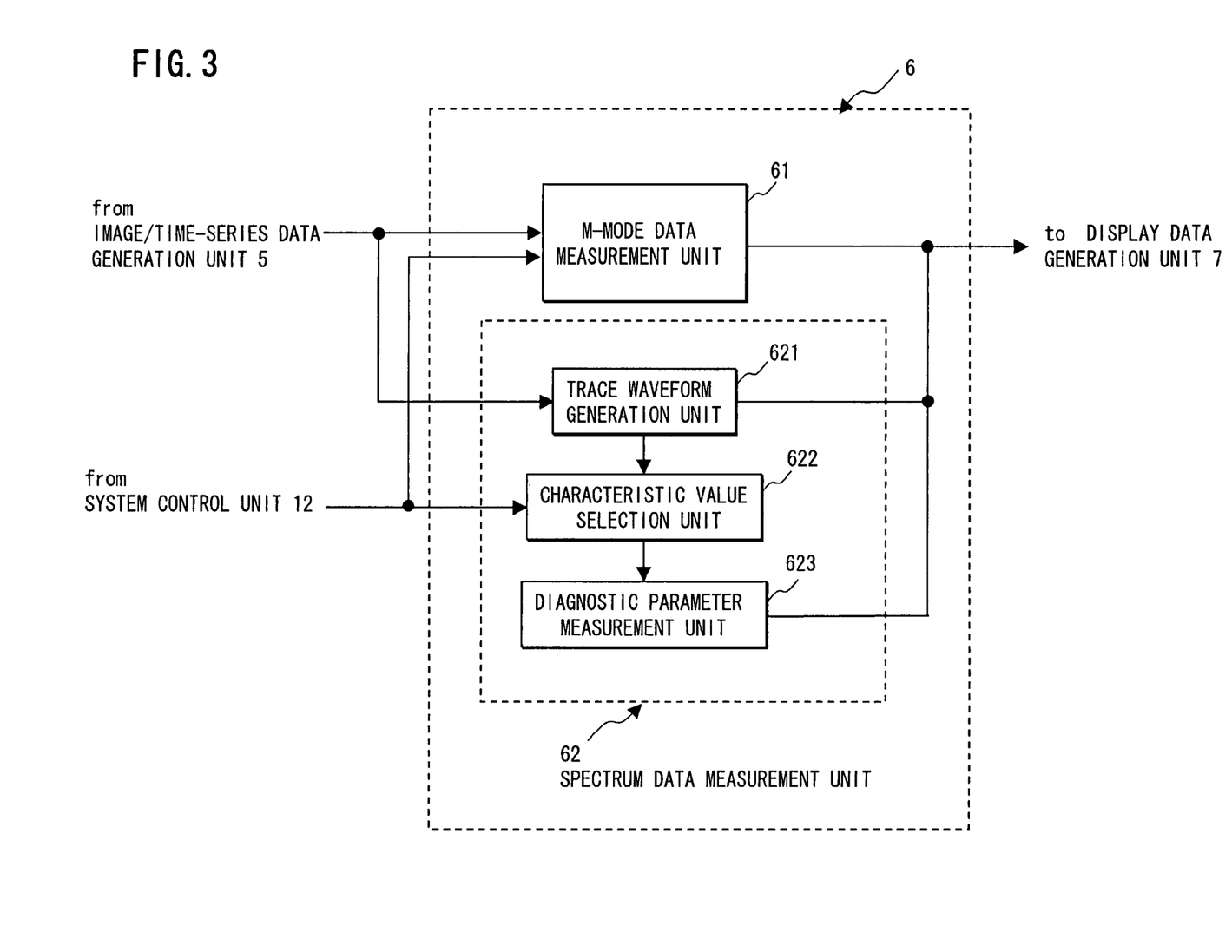
FIG. 3 is a block diagram showing the composition of a time-series data measurement unit in the embodiment shown in FIG. 1.

The composition of an ultrasonic diagnostic apparatus and the basic operation of each unit according to an embodiment of the present invention will be described below with FIG. 1 to FIG. 7. FIG. 1 is a block diagram showing the overall composition of an ultrasonic diagnostic apparatus according to this embodiment. FIG. 2 is a block diagram showing the composition of a transmission/reception unit and a data generation unit. And FIG. 3 is a block diagram showing the composition of a time-series data measurement unit which constitutes the ultrasonic diagnostic apparatus.

An ultrasonic diagnostic apparatus 100 shown in FIG. 1 includes an ultrasonic probe 3 which transmits ultrasound to and receives ultrasound from an object to be examined, a transmission/reception unit 2 which performs transmission/reception with respect to the ultrasonic probe 3, and a data generation unit 4 which generates ultrasonic data such as B-mode data, colored Doppler data and Doppler spectrum on the basis of receiving signals supplied from the transmission/reception unit 2. This ultrasonic diagnostic apparatus 100 further includes an image/time-series data generation unit 5 which generates image data (B-mode image data and colored Doppler image data) by storing the B-mode data and colored Doppler data corresponding to the transmission/reception direction, and generates time-series data (Doppler spectrum data and M-mode data) by storing the Doppler spectrum and B-mode data correspond to a predetermined transmission/reception direction.

Moreover, the ultrasonic diagnostic apparatus 100 includes a time-series data measurement unit 6 which reads the time-series data stored in the image/time-series data generation unit 5 in a predetermined period and measures diagnostic parameters, a display data generation unit 7 which generates display data by combining image data, time-series data and measurement results of diagnostic parameters which are supplied from the image/time-series data generation unit 5 and the time-series data measurement unit 6 on the basis of a predetermined display format, a display format setting unit 8 which sets up the display format for image data and time-series data in a display mode and a measurement mode according to a display format selection signal supplied from the input unit 11, and a display unit 9 which displays the display data generated by the display data generation unit 7.

Furthermore, the ultrasonic diagnostic apparatus 100 includes a reference signal generation unit 1 which generates, for example, continuous wave or rectangular wave having a frequency almost equal to the center frequency of ultrasonic pulses, and supplies it to the transmission/reception unit 2 and the data generation unit 4, an input unit 11 which is used by an operator to, for example, select a display format in the display mode (dynamic image display mode or freeze image display mode), select a display format in measuring mode, switch a display mode, and select measurement items, and a system control unit 12 which systematically controls the respective units of the ultrasonic diagnostic apparatus 100 described above.

The ultrasonic probe 3 has a one-dimensional array of a plurality of (N) minute ultrasonic transducers at the distal end portion and transmits/receives ultrasound to/from the object while the front surface of the probe is in contact with the surface of the object. Each ultrasonic transducer is an electro-acoustic conversion element, which has a function of converting an electrical pulse into an ultrasonic pulse (transmitting ultrasound) at the time of transmission and converting a reflected ultrasound (receiving ultrasound) into an electrical signal (receiving signal) at the time of reception. Each of ultrasonic transducers is connected to the transmission/reception unit 2 through a cable (not shown) The ultrasonic probe 3 includes probes for sector scanning, linear scanning, and convex scanning, one of which is arbitrarily selected in accordance with a diagnosis region. The following description will exemplify the ultrasonic probe 3 for sector scanning suitable for the measurement of cardiac function. However, the ultrasonic probe 3 is not limited to this embodiment, and the probe may be used for linear scanning or convex scanning.

The transmission/reception unit 2 shown in FIG. 2 includes a transmission unit 21 which generates a driving signal for making the ultrasonic probe 3 transmit ultrasound and a reception unit 22 which performs phased addition (addition of receiving signals obtained from a predetermined direction on phase matching) of receiving signals supplied from the ultrasonic probe 3.

As shown in FIG. 2, the transmission unit 21 includes a rate pulse generator 211, a transmission delay circuit 212, and a pulser 213. The rate pulse generator 211 generates a rate pulse for determining the repetition period of transmitting ultrasound by dividing the frequency of continuous wave or rectangular wave supplied from the reference signal generation unit 1, and supplies the rate pulse to the transmission delay circuit 212.

The transmitting delay circuit 212 has independent delay circuits equal in number to the ultrasonic transducers used for transmission. The transmission delay circuit 212 gives delay time to the rate pulse for focusing transmitting ultrasound to a predetermined depth so as to obtain narrow beam width and deflecting transmitting ultrasound in a predetermined direction, and supplies the resultant rate pulse to the pulser 213. The pulser 213 has independent driving circuits corresponding to N channels, and generates driving pulses for driving the ultrasonic transducers on the basis of the timing of the rate pulse.

The reception unit 22 includes a pre-amp (pre-amplifier) 221, an A/D converter 222, a reception delay circuit 223, and an adder 224 each of which correspond to N channels. N-channel receiving signals supplied from the ultrasonic probe 3 are amplified to get sufficient S/N by the pre-amp 221, converted into digital signals by the A/D converter 222 and sent to the reception delay circuit 223.

The reception delay circuit 223 gives delay time for focusing reflected ultrasound from a predetermined depth and setting receiving directivity with respect to a predetermined direction to each of the N-channel receiving signals output from the A/D converter 221. The adder 223 performs the phased addition of receiving signals from the reception delay circuit 223.

The data generation unit 4 includes a B-mode data generation unit 41 which generates B-mode data with respect to the receiving signal output from the adder 224 of the reception unit 22, a Doppler signal detection unit 42 which detects Doppler signals by performing quadrature detection to the receiving signal, a colored Doppler data generation unit 43 which generates colored Doppler data on the basis of the detected Doppler signals, and a spectrum generation unit 44 which generates frequency spectrum with respect to the Doppler signal.

As illustrated in FIG. 2, the B-mode data generation unit 41 includes an envelope detector 411 and a logarithmic converter 412. The envelope detector 411 performs envelope detection of the receiving signal after phased addition which is supplied from the adder 224 of the reception unit 22. The amplitude of this envelope detection signal is logarithmically converted by the logarithmic converter 412. The Doppler signal detection unit 42 has a n/2 phase shifter 421, mixers 422-1 and 422-2, LPFs (Low-Pass Filters) 423-1 and 423-2, and detects Doppler signals by performing quadrature phase detection for the receiving signal supplied from the adder 224 of the reception unit 22.

The colored Doppler data generation unit 43 includes a Doppler signal storage circuit 431, an MTI filter 432 and an autocorrelation calculation unit 433, and the Doppler signals output from the Doppler signal detection unit 42 are stored in the Doppler signal storage circuit 431. The MTI filter 432 which is a digital low pass filter reads the Doppler signals stored in the Doppler signal storage circuit 431, and removes the clutter component of the Doppler signals resulting from a respiratory movement or a pulsatile movement of an organ. The autocorrelation calculation unit 433 calculates an autocorrelation coefficient of the Doppler signal includes only blood-flow information, and calculates average blood flow velocity and a variance of the blood flow velocity on the basis of the autocorrelation coefficient.

The spectrum generation unit 44 includes a SH (sample/hold circuit) 441, an LPF (low pass filter) 442 and an FFT (fast Fourier transform) analyzer 444, and performs FFT analysis with respect to the Doppler signals obtained by the Doppler signal detection unit 42. Note that, the SH 441 and the LPF 442 have two channels, to each of which the complex components (i.e., a real component and imaginary component) of the Doppler signals output from the Doppler signal detection unit 42 are supplied.

The Doppler signals output from the LPFs 423-1 and 423-2 of the Doppler signal detection unit 42 and a sampling pulse (range gate pulse) generated by the system control unit 12 by frequency-dividing the reference signal from the reference signal generation unit 1 are supplied to the SH 441. Note that, the sampling pulse is generated with a delay time Ts after the rate pulse which determines the timing of transmitting ultrasound. The delay time Ts can be arbitrarily set in the input unit 11. By changing the delay time Ts of the sampling pulse, a Doppler signal at a desired distance Lg from the ultrasonic probe 3 can be extracted. Note that, letting C be the ultrasound velocity in the object, the delay time Ts and desired distance Lg have the relationship represented by 2Lg/C=Ts.

A staircase noise component superimposed on the Doppler signal at the desired distance Lg output from the SH 441 is removed by the LPF 442, and the Doppler signal is smoothed. The FFT analyzer 443 includes a calculation circuit and storage circuit (not shown). The calculation circuit reads the Doppler signal stored in the storage circuit and performs FFT analysis of the Doppler signal in a predetermined period and generates a Doppler spectrum.

Referring back to FIG. 1, the image/time-series data generation unit 5 stores B-mode data and colored Doppler data generated by the data generation unit 4 corresponding to the transmission/reception direction to generate B-mode image data and colored Doppler image data.

Furthermore, the image/time-series data generation unit 5 stores serially the B-mode data obtained by repetition of the transmission/reception to a desired direction Ox and generates M-mode data. Similarly, the image/time-series data generation unit 5 stores serially the Doppler spectrum obtained by repetition of the transmission/reception to θx, and generates Doppler spectrum data. That is, a plurality of B-mode image data and colored Doppler image data are stored in an image data storage area and a plurality of M-mode data and Doppler spectrum data are stored in a time-series data storage area of the image/time-series data generation unit 5.

The example of the time-series data measurement unit 6 which measures various diagnostic parameters by using the time-series data stored in the image/time-series data generation unit 5 will be described with reference to the block diagram shown in FIG. 3. The time-series data measurement unit 6 has an M-mode data measurement unit 61 for measuring diagnostic parameters based on the M-mode data and a spectrum data measurement unit 62 for measuring diagnostic parameters based on the Doppler spectrum data. And, the spectrum data measurement unit 62 includes, for example, a trace waveform generation unit 621, a characteristic value selection unit 622, and a diagnostic parameter measurement unit 623.

The trace waveform generation unit 621 reads the Doppler spectrum data in a predetermined period stored in the image/time-series data generation unit 5 according to the selection information for measuring items supplied from the input unit 11 through the system control unit 12, and generates a trace waveform of the maximum blood flow velocity corresponding to the maximum frequency of the Doppler spectrum data.

The characteristic value selection unit 622 selects, for example, E-wave (early diastoric blood flow wave) and A-wave (atrial contraction blood flow wave) of the trace waveform displayed on the display unit 9 in the left ventricle inflow measurement according to a command signal from the input unit 11, and supplies the position (time) information of E-wave and A-wave to the diagnostic parameter measurement unit 623.

On the other hand, the diagnostic parameter measurement unit 623 includes a calculation circuit (not shown in the figure) and measures characteristic parameters [E/A] and [DCT (deceleration time)] based on the trace waveform of the maximum blood flow velocity supplied from the trace waveform measurement unit 621 and the position information of E-wave and A-wave of the trace waveform supplied from the characteristic value selection unit 622.

Figure 4:
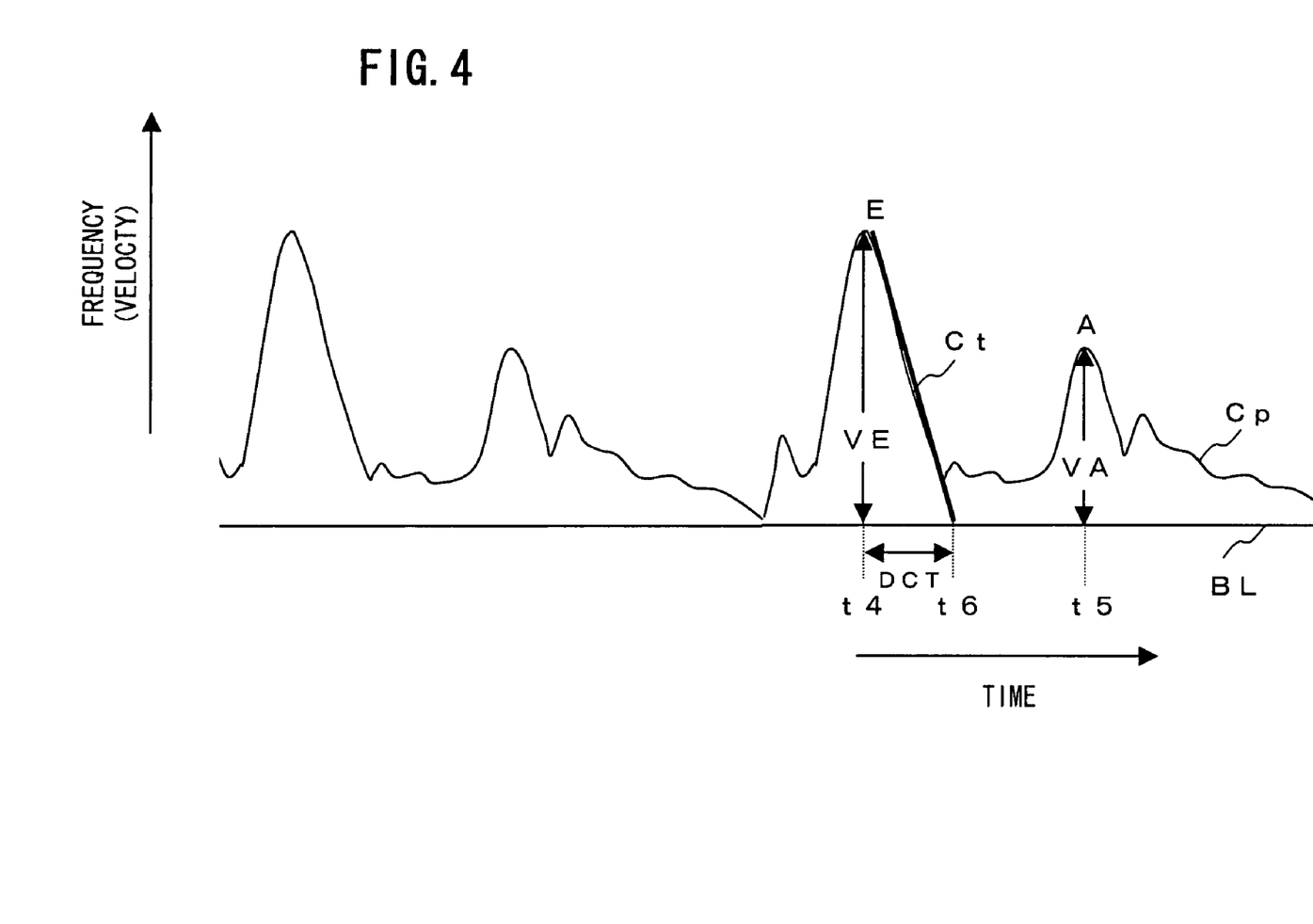
FIG. 4 is a diagram showing an example of the diagnostic parameter measurement in the embodiment shown in FIG. 1.

An example of the diagnostic parameter measurement performed by the diagnostic parameter measurement unit 623 with respect to the trace waveform of the maximum blood flow velocity generated by the trace waveform generation unit 621 of the spectrum data measurement unit 62 will be described with reference to the diagram shown in FIG. 4. FIG. 4 shows the trace waveform Cp for 2 cardiac cycles displayed on the display unit 9. The calculating circuit of the diagnostic parameter measurement unit 623 measures the diagnostic parameter [E/A] based on the ratio of E-wave amplitude VE at time t4 and A-wave amplitude VA at time t5. Note that, A-wave and E-wave are selected with respect to the trace waveform Cp by the characteristic value selection unit 622.

Subsequently, the calculation circuit of the diagnostic parameter measurement unit 623 sets a tangent Ct to a downward curve from the maximum of E-wave, and measures the diagnostic parameter [DCT] based on the interval between time t4 of E-wave and time t6 where the tangent Ct crosses a baseline BL. In this FIG. 4, for simplicity of illustration, a case where the display period is 2 cardiac cycles, however trace waveform having 4 cardiac cycles to 8 cardiac cycles is usually used. Note that the M-mode data measurement unit 61 of the time-series data measurement unit 6 has the same function as the spectrum data measurement unit 62. And the M-mode data measurement unit 61 measures diagnostic parameters such as LVV (left ventricle volume), EDV (end diastolic volume) ESV (end systolic volume), CO (cardiac output), EF (ejection fraction), etc, but its detailed description will be omitted.

The display data generation unit 7 shown in FIG. 1 generates display data on the basis of a predetermined display format corresponding to each of the dynamic image display mode for setting the ROI and the freeze image display mode for measuring the diagnostic parameters with respect to the time-series data obtained from an area corresponding to the ROI. That is, in the dynamic image display mode, the display data generation unit 7 reads the time-series data (M-mode data or Doppler spectrum data) in a predetermined period stored in the image/time-series data generation unit 5 and generates time-series data using a scroll method or a moving bar method.

Subsequently, the display data generation unit 7 reads the image data (B-mode image data or colored Doppler image data) obtained at the time correspond to the end portion of the time-series data or the position of moving bar shown on the time-series data. And the display data generation unit 7 generates a display data by compounding the time-series data and image data based on the display format information of the dynamic image display mode supplied from the display format setting unit 8.

On the other hand, in the freeze image display mode, the display data generation unit 7 generates display data by compounding the time-series data and image data correspond to the timing of switching signal for changing from the dynamic image display mode to the freeze image display mode supplied from the input unit 11 through the system control unit 12. Furthermore, when diagnostic parameters are measured in the freeze image display mode, the display data generation unit 7 compounds the image data and the time-series data on the basis of predetermined display format of the measurement mode correspond to the measurement item selection information supplied from the input unit 11, and generates display data by superimposing a trace waveform and measurement results of the diagnostic parameter on the compounded data.

The display format setting unit 8 includes a storage circuit (not shown in the figure). And various display format information are pre-stored in the storage circuits. Furthermore, the display format selection information supplied from the input unit 11 through the system control unit 12 is also stored in the storage circuit. And the display format setting unit 8 reads display format information of the dynamic image display mode, the freeze image display mode and the measurement mode correspond to the display format selection information in the display mode and the measurement mode supplied from the input unit 11 through the system control unit 12 and supplies it to the display data generation unit 7.

FIG. 5 shows schematically examples of the display format information pre-stored in the storage circuit of the display format setting unit 8. For example, FIG. 5A shows a display format in which display data is constituted by time-series data 81. FIG. 5B and FIG. 5C show display formats of a UP/Down display form in which the time-series data 81 and the image data 82 are arranged in a vertical direction and FIG. 5D shows a display format of a Left/Right display form in which the time-series data 81 and the image data 82 are arranged in a left-and-right direction. Note that, FIG. 5B shows a display format in which display height h1 of the image data 82 and display height h2 of the time-series data are at almost equal, and FIG. 5C shows a display format in which display height h2 of the time-series data 81 is larger than display height h1 of the image data 82 (for example, h2/h1=3).

The display unit 9 shown in FIG. 1 includes a conversion circuit and a monitor (not shown). The conversion circuit performs D/A conversion and TV format conversion with respect to the display data generated by the display data generation unit 7, and displays it on the monitor.

Figure 6:
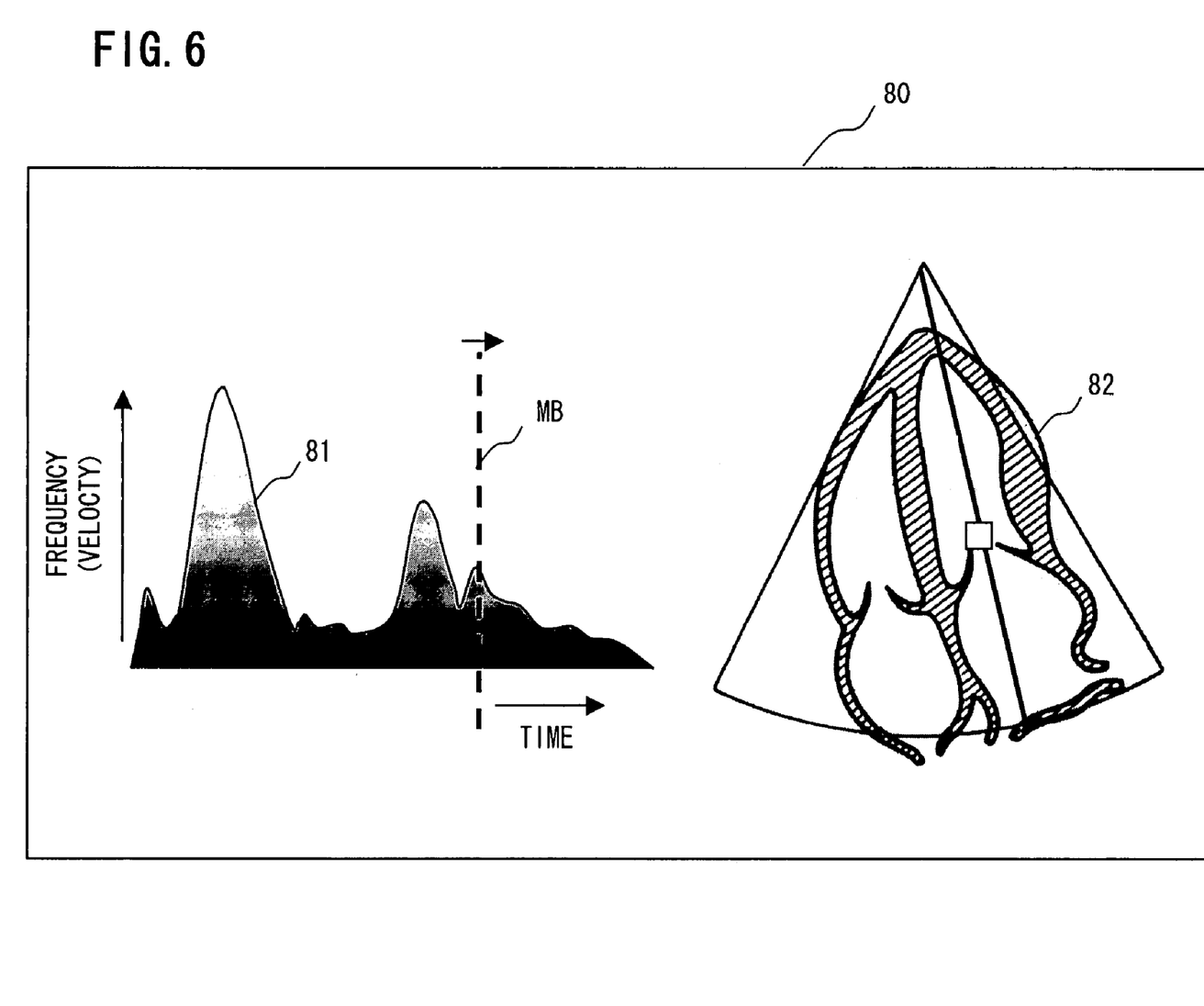
FIG. 6 is a diagram showing an example of display data in a dynamic image display mode of the embodiment shown in FIG. 1.

FIG. 6 shows an example of the display data displayed on the monitor of the display unit 9 in the dynamic image display mode. The time-series data (Doppler spectrum data) 81 in a predetermined period are displayed on the left domain of the display data 80 with the moving bar method, and the image data (B-mode image data) 82 correspond to the moving bar MB of the time-series data 81 is displayed on the right domain of the display data 80. And this image data 82 is displayed as a dynamic image with movement of the moving bar MB.

Figure 5A:
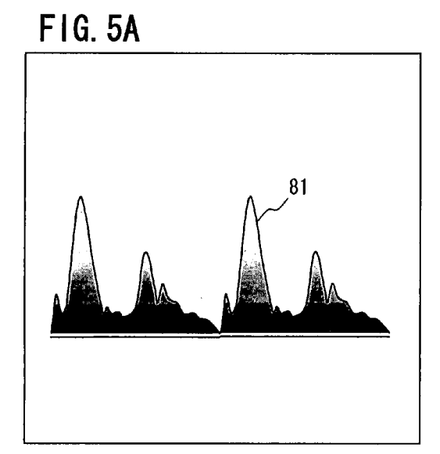
FIG. 5A to FIG. 5D are schematic diagrams showing examples of the display format information pre-stored in a display format setting unit in the embodiment shown in FIG. 1.
Figure 5B:
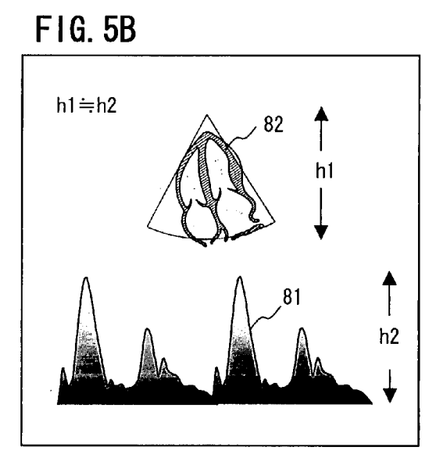
Figure 5C:
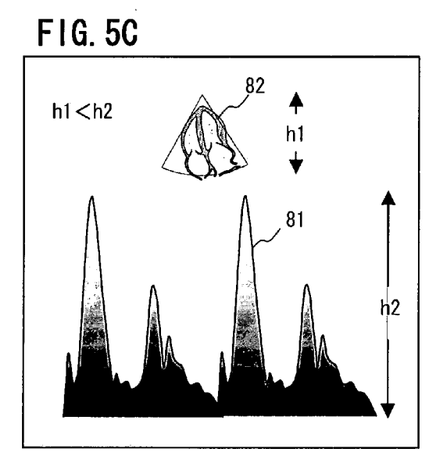
Figure 5D:
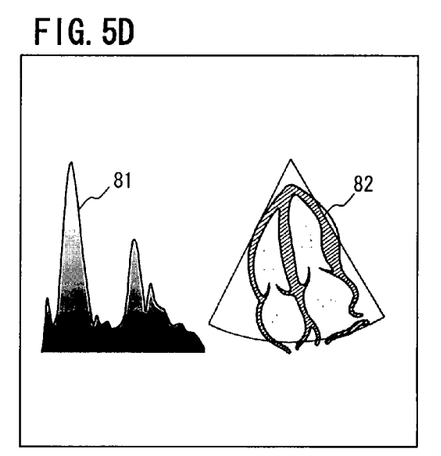

In this case, the display format setting unit 8 reads display format information corresponding to FIG. 5D from the storage circuit of self on the basis of the display format selection information for the dynamic image display mode supplied from the input unit 11, and supplies it to the display data generation unit 7. On the other hand, the display data generation unit 7 generates display data by compounding the image data and the time-series data supplied from the image/time-series data generation unit 5 based on the display format information described above, and supplies it to the display unit 9.

Figure 7:
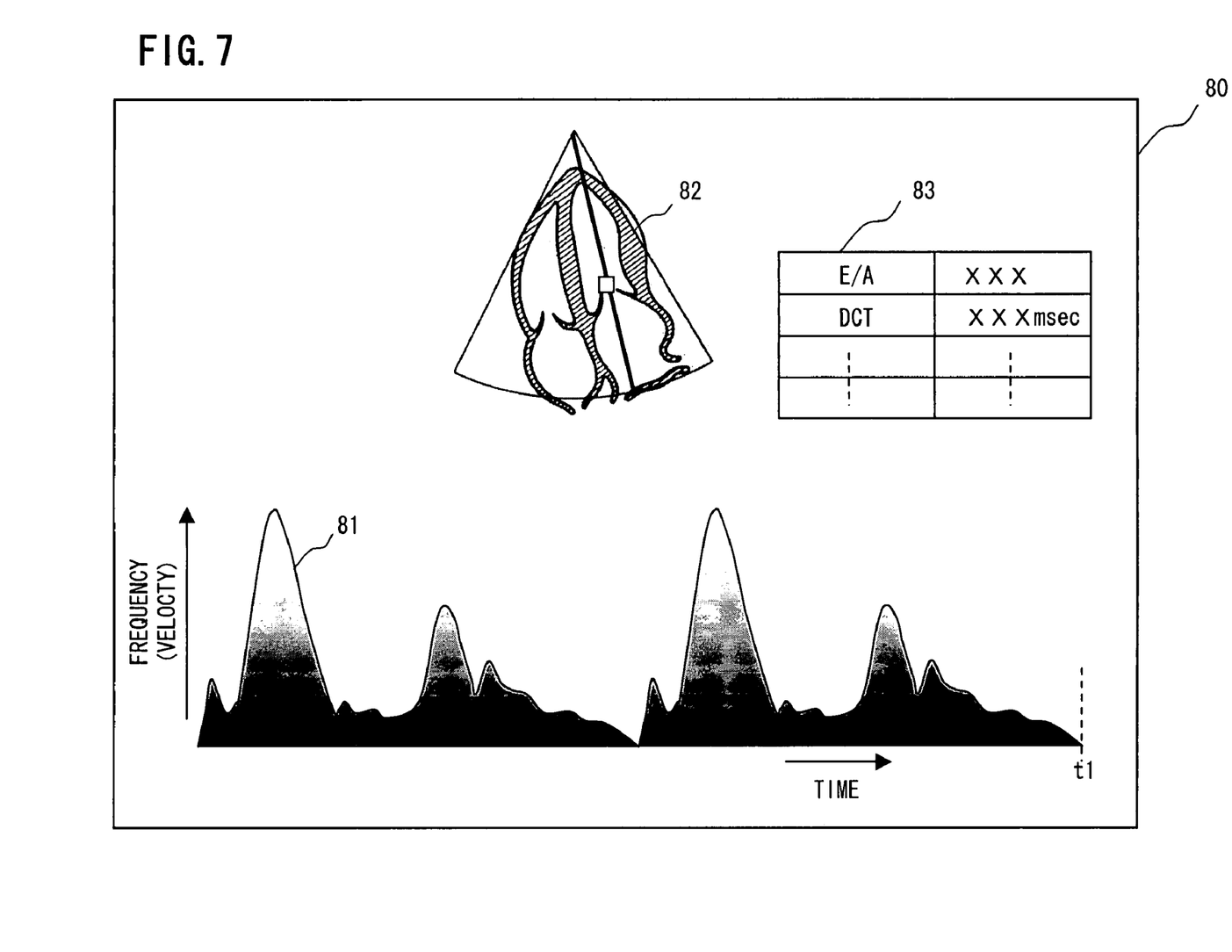
FIG. 7 is a diagram showing an example of display data in a freeze image display mode of the embodiment shown in FIG. 1.

FIG. 7 shows an example of the display data displayed on the monitor of the display unit 9 in the freeze image display mode. The time-series data (Doppler spectrum data) 81, for example, in a predetermined period to timing t1 when a switching signal for changing from the dynamic image display mode to the freeze image display mode is inputted is displayed on the lower domain of the display data 80. And the image data (B-mode image data) 82 obtained at timing t1 is displayed on the upper domain of the display data 80 as freeze image.

In this case, the display format setting unit 8 reads display format information corresponding to FIG. 5B or FIG. 5C from the storage circuit of self on the basis of the display format selection information for the freeze image display mode supplied from the input unit 11, and supplies it to the display data generation unit 7. On the other hand, the display data generation unit 7 reads the time-series data in the predetermined period to the timing t1 when the display mode switching signal (i.e., switching signal for changing from the dynamic image display mode to the freeze image display mode) is inputted and the image data obtained at timing t1 from the image/time-series data generation unit 9. The display data generation unit 7 generates the display data by compounding the image data and the time-series data based on the display format information described above. And the display data is displayed on the monitor of the display unit 9.

In the measurement of diagnostic parameters by using the time-series data in the freeze image display mode, the measurement result of the diagnostic parameters obtained by the time-series data measurement unit 6 in the measurement mode is displayed while being superimposed on the compounded data described above. Although FIG. 7 shows a case where the same display format is selected in the freeze image display mode and in the measurement mode, different display format may be selected. In the dynamic image display mode for setting the ROI to the time-series data, the display format of the Left/Right display form (refer to FIG. 6) capable of displaying wide image data with high setting accuracy is usually selected. Moreover, in the freeze image display mode and the measurement mode for measuring the diagnostic parameters in the time-series data, the display format of the Up/Down display form (refer to FIG. 7) capable of displaying wide time-series data in a left-and-right direction is selected.

The input unit 11 shown in FIG. 1 is an interactive interface having a display panel and input devices such as a trackball, a mouse, and selection buttons on an operation panel, and is used to input patient information, set generation conditions of image data and time-series data, select image data and time-series data in the measurement of diagnostic parameters, input various command signals, etc.

The input unit 11 includes a display mode switching unit 111 configured to input a display mode switching signal for the dynamic image display mode and the freeze image display mode, a region of interest (ROI) setting unit 112 configured to set a ROI on the image data, display format selection unit 113 configured to select the display format and a measurement item selection unit 114 configured to select desired measurement item(s) from a plurality of measurement items for the time-series data.

Moreover, the input unit 11 is used to designate positions of E-wave and A-wave on the trace waveform of the freeze image data displayed on the display unit 9.

The system control unit 12 includes a CPU and a storage circuit (not shown). The input information, setting information, and selection information supplied from the input unit 11 are stored in the storage circuit. And the CPU systematically controls the respective units of the ultrasonic diagnostic 100 and the overall system based on the above information supplied from the input unit 11.

(Procedure for Generating and Displaying Time-Series Data)

A procedure for generating and displaying time-series data in this embodiment will be described with reference to a flow chart shown in FIG. 8.

Figure 8:
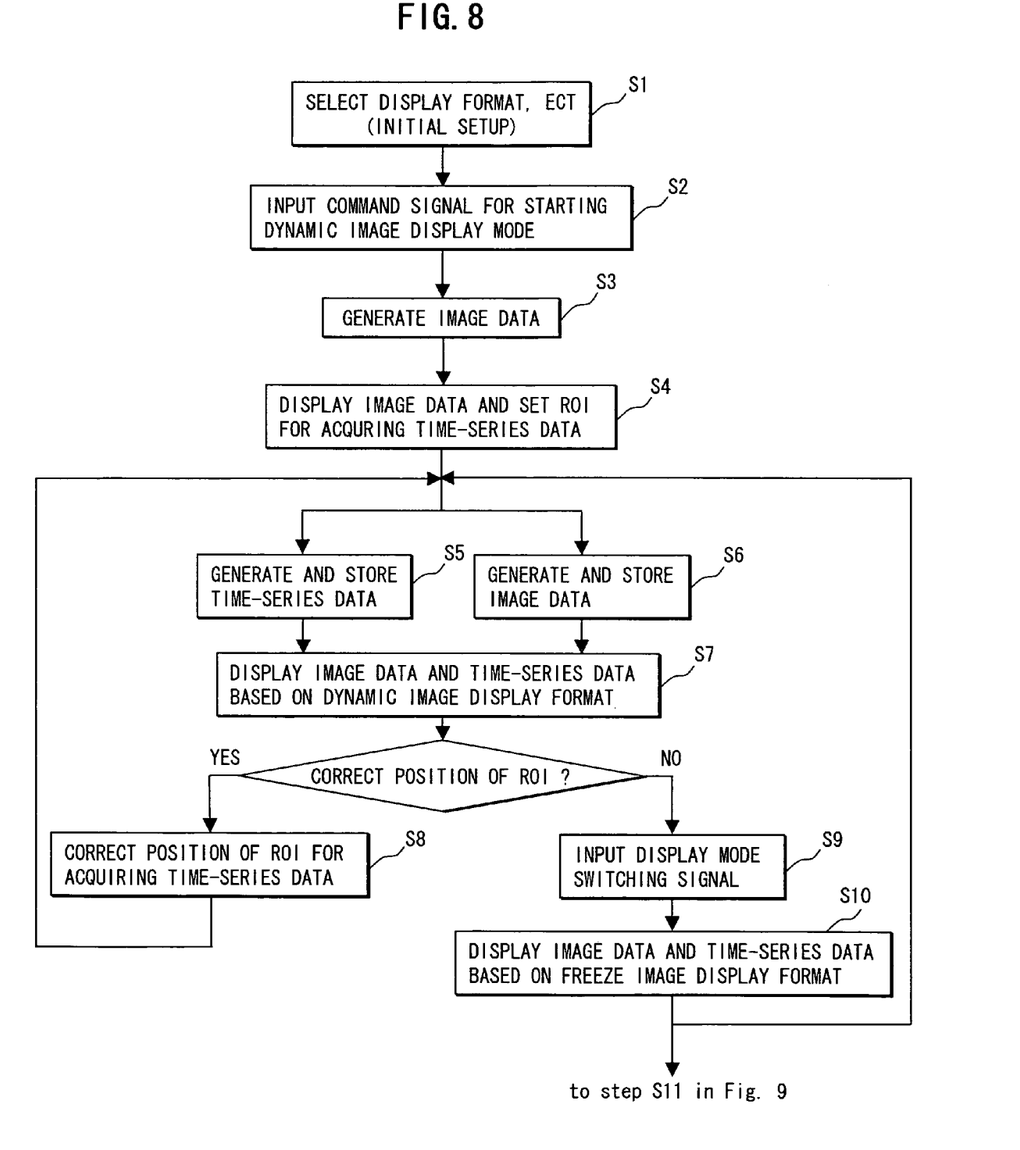
FIG. 8 is a flow chart illustrating a procedure in which image data and time-series data are generated and displayed in the embodiment shown in FIG. 1.

Prior to the transmission/reception of ultrasound with respect to an object to be examined, an operator operates the input unit 11 to input patient information, select the display format in the dynamic image display mode and the freeze image display mode, select the display format in the measurement mode, set generation conditions of image data and time-series data, select image data and time-series data in the diagnostic measurement The input information, setting information, and selection information described above are stored in the storage circuit of the system control unit 12. furthermore the display format selection information of the dynamic image display mode and the freeze image display mode and the display format selection information of the measurement mode are stored in the storage circuit of the display format setting unit 8 (step S1 in FIG. 8).

Note that, the following explanation describe the case in which a Left/Right display form (FIG. 5D) as a display format of the dynamic image display mode and a Up/Down display form (FIG. 5B) as a display format of the freeze image display mode and the measurement mode are selected, and the B-mode data and the Doppler spectrum data as image data and the time-series data in the diagnostic parameter measurement are selected. However, another display format or another image data and time-series data may be selected.

When the initial setting described above are complete, the operator inputs a command signal for starting the dynamic image display mode in the input unit 11 (step S2 in FIG. 8) and fixes the ultrasonic probe 3 at a desired position on the body surface of the object. Then ultrasonic transmission/reception is then performed in the first transmission/reception direction θ1 and the B-mode data corresponding to the direction is generated. That is, the rate pulse generator 211 of the transmission/reception unit 2 receives the command signal through the system control unit 12, frequency-divides the reference signal supplied from the reference signal generation unit 1 to generate a rate pulse for determining the repetition period of ultrasonic pulses transmitted into the object, and supplies the rate pulse to the transmission delay circuit 212.

The transmission delay circuit 212 gives the rate pulse focusing delay time for focusing ultrasound to a predetermined depth and deflection delay time for transmitting ultrasound in the direction θ1, and supplies the rate pulse with delay time described above to the pulser 213. The pulser 213 then generates a driving signal based on the timing of the rate pulse and supplies the driving signal to the ultrasonic transducers of the ultrasonic probe 3 through a cable (not shown) to transmit an ultrasonic pulse in the direction θ1.

The ultrasonic pulse transmitted to the object is partially reflected at the boundary surfaces between organs or tissues having different acoustic impedances. Furthermore, the ultrasonic frequency is Doppler-shifted when the ultrasound is reflected at moving reflectors such as cardiac wall or blood cells.

The reflected ultrasound (receiving ultrasound) from tissue or blood cells in the object is received by the ultrasonic transducers of the ultrasonic probe 3 to be converted into electrical signals (receiving signals). The receiving signals are amplified by the N-channel pre-amp 221 and converted into digital signals by the N-channel A/D converter 222 in the reception unit 22. The receiving delay circuit 223 gives the receiving signals converted into the digital signals predetermined delay time and the receiving signals with the delay time are added by the adder 224. The output signal of the adder 224 is then supplied to the B-mode data generation unit 41 of the data generation unit 4.

At this time, in the receiving delay circuit 222, delay time for focusing reflected ultrasound to predetermined depth and delay time for having strong receiving directivity in the direction θ1 are set to the reflected ultrasound according to a control signal from the system control unit 12. The output signal from the adder 224 is performed envelope detection and logarithmic conversion in the B-mode data generation unit 41 of the data generation unit 4 and the resultant signal is stored in the image data storage area of the image/time-series data generation unit 5.

The system control unit 12 performs ultrasound transmission/reception in directions θ2 to θp according to the same sequence and the B-mode data obtained at this time are stored in the image data storage area. That is, the B-mode data corresponding to the directions θ1 to θP are sequentially stored in the image data storage area of the image/time-series data generation unit 5 to generate B-mode image data corresponding to one frame (step S3 in FIG. 8).

On the other hand, the display data generation unit 7 generates display data by transforming the B-mode image data generated in the image/time-series data generation unit 5. The conversion circuit of the display unit 9 generates a video signal by performing D/A conversion and TV format conversion of the display data and the video signal is displayed on the monitor of the display unit 9. Subsequently, ultrasonic transmission/reception is repeated in the directions θ1 to θP in the same manner as described above, and the B-mode image data generated based on the receiving signal are displayed on the display unit 9 in real time.

The operator sets a Doppler marker in a direction θx with respect to the B-mode image data displayed on the monitor of the display unit 9 and sets a range gate at the position of distance Lg on this Doppler maker for acquiring Doppler spectrum (step S4 in FIG. 8). At this time, the system control unit 12 controls transmitting delay time in the transmitting delay circuit 212 of the transmission unit 21 and receiving delay time in the receiving delay circuit 223 of the reception unit 22 and performs ultrasonic transmission/reception in the directions θ1 to θP for acquiring B-mode data and in a direction θx correspond to the Doppler maker for acquiring Doppler spectrum.

The Doppler signal detection unit 42 detects Doppler signals by quadrature phase detection of the receiving signal, and supplies it to the SH 441 of the spectrum generation unit 44. The SH 441 samples and holds Doppler signals by using a sampling pulse correspond to the range gate supplied from the system control unit 12. And the output signal of the SH 441 while repeating ultrasonic transmission/reception in the direction θx are smoothed by the LPF 442 and stored in the storage circuit of the FFT analyzer 443.

The calculating circuit of the FFT analyzer 443 generates Doppler spectrum by performing FFT analysis of the Doppler signal time-serially obtained by repeating ultrasonic transmission/reception and stores it in the time-series data storage area of the image/time-series data generation unit 5. That is, the Doppler spectrum is time-serially stored in the time-series data storage area of the image/time-series data generation unit 5 to generate Doppler spectrum data (step S5 in FIG. 8).

On the other hand, B-mode data generation unit 41 of the data generation unit 4 generates B-mode data based on the receiving signal obtained by ultrasonic transmission/reception in the directions θ1 to θp which alternately performed to the ultrasonic transmission/reception in the direction θx. And the B-mode data are stored the image data storage area of the image/time-series data generation unit 5 correspond to the transmission/reception direction and a plurality of B-mode data are sequentially arrayed to generate B-mode image data (step S6 in FIG. 8). The display format setting unit 8 reads the display format information shown in FIG. 5D from the storage circuit of self according to the display format selection information already supplied from the display format selection unit 113 of the input unit 11, and supplies it to the display data generation unit 7 as a display format in the dynamic image display mode.

The display data generation unit 7 reads the Doppler spectrum data in the predetermined period and the B-mode image data at the time corresponding to the moving bar shown on the Doppler spectrum data supplied from the image/time-series data generation unit 5, and generates display data in the dynamic image display mode on the basis of the display format information supplied from the display format setting unit 8. And the display data generated by the display data generation unit 7 is displayed on the monitor of the display unit 9 in real time (refer to FIG. 6) (step S7 in FIG. 8).

Subsequently, the operator judges the validity of the ROI set on the B-mode image data by referring to the B-mode image data and the Doppler spectrum data in the display data displayed on the display unit 9. And when the ROI needs to be corrected, the position of the ROI displayed on the monitor of the display unit 9, i.e., the position of range gate, is changed by using the input device of the input unit 11 (step S8 in FIG. 8), and the procedure of step S5 to step S7 mentioned above is repeated.

On the other hand, when the correction is not necessary, the display mode switching signal for changing from the dynamic image display mode to the freeze image display mode is inputted in the display mode switching unit 111 of the input unit 11 (step S9 in FIG. 8). The display format setting unit 8 receives this display mode switching signal through the system control unit 12 and reads the display format information shown in FIG. 5B from the storage circuit of self on the basis of the display format selection information already supplied from the display format selection unit 113 of the input unit 11, and supplies it to the display data generation unit 7 as a display format in the freeze image display mode.

The display data generation unit 7 reads the time-series data in the predetermined period to the timing t1 when the display mode switching signal is inputted in the display mode switching unit 111 of the input unit 11 and the image data obtained at timing t1 from the image/time-series data generation unit 5, and compounds these data based on the display format information in the freeze image display mode to generates display data. And the display data is displayed on the display unit 9 (step S10 in FIG. 8). Moreover, when observing of the image data and the time-series data in the dynamic image display mode is again needed, the operator inputs the display mode switching signal for changing from the freeze image display mode to the dynamic image display mode in the display mode switching unit 111, and the procedure of step S5 to S10 mentioned above are repeated according to the display mode switching signal.

(Measurement Procedure of Diagnostic Parameters)

A procedure for measuring diagnostic parameters in this embodiment will be described with reference to a flow chart shown in FIG. 9.

Figure 9:
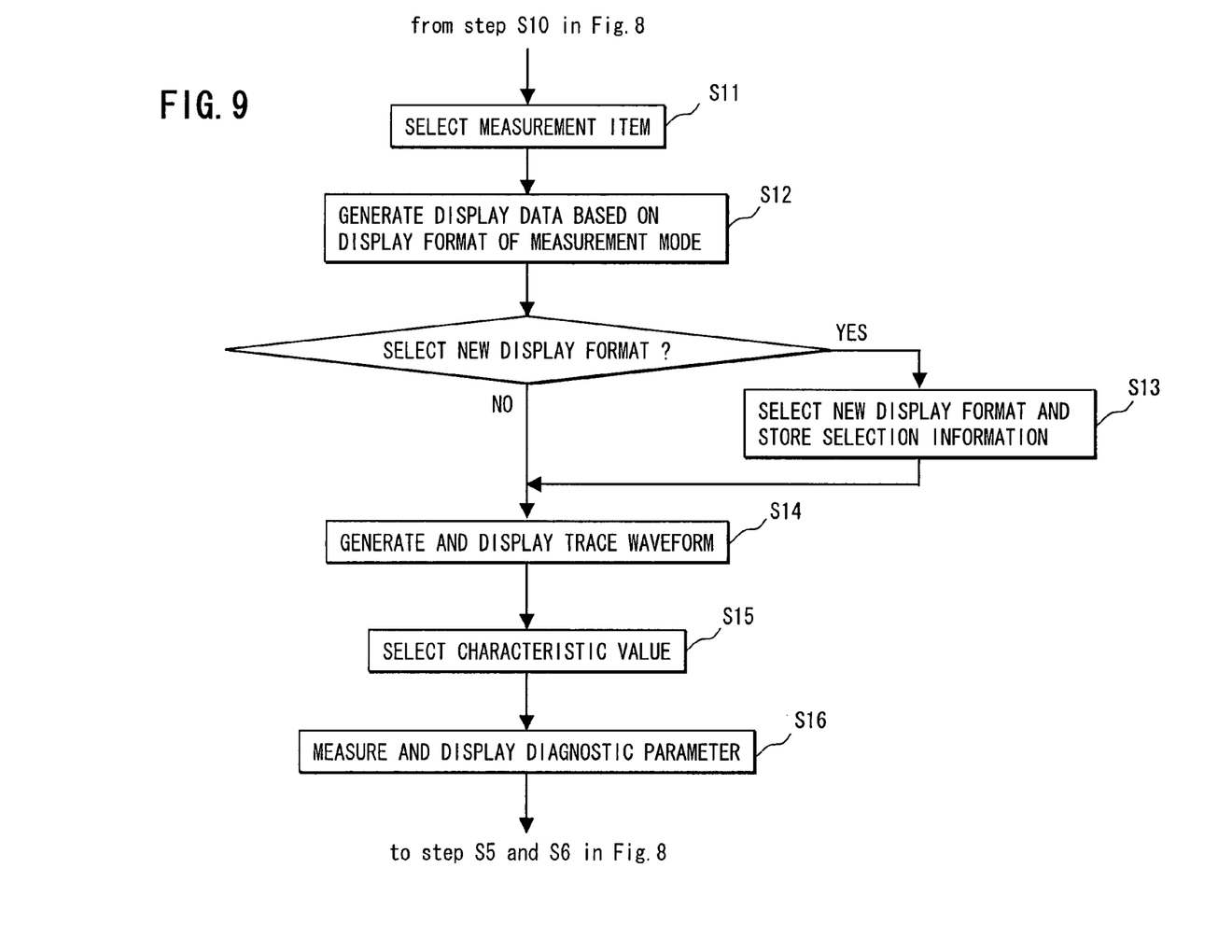
FIG. 9 is a flow chart illustrating a procedure in which diagnostic parameters are measured in the embodiment in FIG. 1.

The operator who observed the display data in the freeze image display mode displayed on the display unit 9 in step 10 shown in FIG. 8 selects the desired measurement item in the measurement item selection unit 114 of the input unit 11 (step S11 in FIG. 9). This selection information (measurement item selection information) is supplied to the display format setting unit 8, the display data generation unit 7 and the time-series data measurement unit 6 through the system control unit 12. The display format setting unit 8 which received this measurement item selection information reads the predetermined display format information with respect to the measurement item, for example, shown in FIG. 5B from the storage circuit of self, and supplies it to the display data generation unit 7 as a display format information in the measurement mode.

The display data generation unit 7 reads again the image data and the time-series data which are used for generating the display data in the freeze image display mode in step S10 of FIG. 8 from the image/time-series data generation unit 5, and generates the display data based on the display format information in the measurement mode supplied from the display format setting unit 8. And this display data is displayed on the monitor of the display unit 9 (step S12 in FIG. 9). Although, FIG. 7 shows the example where the same display format is selected with respect to the freeze image display mode and the measurement mode, different display format may be selected.

Moreover, if the display format of the display data displayed on the display unit 9 in step S12 is not opportune for measuring diagnostic parameter, the display format may be changed to new display format for this measurement item in the display format selection unit 113 of the input unit 11 by the operator. That is, if the display format of the measurement mode (for example, FIG. 5B) with respect to the measurement item selected in step S1 is not desirable, other display formats (for example, FIG. 5 (c)) is newly selected. And this new selection information of display format is stored in the storage circuit of the display format setting unit 8 (step S13 in FIG. 9).

Subsequently, the trace waveform generation unit 621 of the spectrum data measurement unit 62 in the time-series data measurement unit 6 generates the trace waveform with respect to the highest flow velocity corresponding to the maximum frequency of the time-series data, and supplies it to the display data generation unit 7. The display data generation unit 7 superimposes the trace waveform on the time-series data, and these data are displayed on the monitor of the display unit 9 (step S14 in FIG. 9).

The operator sets the position of E-wave and A-wave on the trace waveform superimposed on the time-series data by using the input device in the input unit 11. On the other hand, the characteristic value selection unit 622 selects E-wave and A-wave on the trace waveform based on the position information on E-wave and A-wave supplied from the input unit 11 through the system control unit 12, and supplies the selection information on E-wave and A-wave to the diagnostic parameter measurement unit 623 (step S15 in FIG. 9).

And the diagnostic parameter measurement unit 623 performs measurement of diagnostic parameter "E/A" and "DCT" based on the trace waveform with respect to maximum flow velocity supplied from the trace waveform generation unit 621 and the selection information on E-wave and A-wave on the trace waveform supplied from the characteristic value selection unit 622. The measurement result of the diagnostic parameter is supplied to the display data generation unit 7, and is compounded with the image data and the time-series data on which the trace waveform is superimposed and these data are displayed on the display unit 9 (refer to FIG. 7), (step S16 of FIG. 9).

Then, the operator inputs the display mode switching signal for changing from the measurement mode to the dynamic image display mode or the freeze image display mode into the display mode switching unit 111 of the input unit 11, and the procedure of step S5 to step S16 or the procedure of step S9 to step S16 are repeated. At this time, the display format in the display mode in step S12 is set on the basis of the newest display format selection information already stored in the storage circuit of the display format setting unit 8.

According to the embodiment described above, when the ROI is set on the image data in the dynamic image display mode and the time-series data is generated based on the receiving signal corresponding to the ROI and various diagnostic parameters are measured based on the time-series data in the freeze image display mode, the display format is automatically updated to suitable display format according to the display mode switching signal or measurement item selection information supplied from the input unit 11. Therefore, diagnostic efficiency is improved and the load on an operator can be remarkably reduced.

Moreover, as the display format in the dynamic image display mode, the freeze image display mode and the measurement mode can be predetermined prior to the inspection; the display format is arbitrarily set according to a diagnosis region of the object, an inclination of the operator, etc. And the diagnosis efficiency and diagnosis accuracy can be improved and the operator's load can be reduced.

Furthermore, the display format in the dynamic image display mode, the freeze image display mode and the measurement mode can be set based on the format information selected arbitrarily from a plurality of display format information pre-stored, a suitable display format can be set efficiently.

In addition, when the dynamic image display mode, the freeze image display mode and the measurement mode are time-serially repeated, the display format in the measurement mode or in the display mode is automatically set based on the newest display format selection information already stored in the storage circuit of the display format setting unit. Therefore, a suitable display format can be set efficiently.

An embodiment of the present invention has been described so far, the invention is not limited thereto. Rather, they may be modified in implementing them. For example, the Up/Down display form is selected as a display format in the dynamic image display mode and the Left/Right display form is selected as a display format in the freeze image display mode in the embodiment described above, it is not limited to this.

Moreover, the case where the time-series data is displayed on the left domain of the display data and the image data is displayed on the right domain of the display data in the Left/Right display form and the time-series data is displayed on the lower domain of the display data and the image data is displayed on the upper domain of the display data in the Up/Down display form has been described, the position of the time-series data and the image data may be changed.

On the other hand, the switching from the display format of the dynamic image display mode to the display format of the freeze image display mode is performed based on the display mode switching signal and the switching from the display format of the freeze image display mode to the display format of the measurement mode is performed based on the measurement item selection information in the embodiment described above. However, the switching from the display format of the dynamic image display mode to the display format of the measurement mode based on the measurement item selection information may be carried out. In this case, the image data or time-series data in the measurement mode are not limited to the freeze image data, and may be the dynamic image data.

Moreover, the case where display data is generated by using the image data and the time-series data in the measurement mode has been described, the display data may be generated by using at least on one of the image data and time-series data.

Numerous modifications and variations of the present invention are possible in light of the above teachings. It is therefore to be understood that, within the scope of the appended claims, the present invention can be practiced in a manner other than as specifically described herein.

What is claimed is:

1. An ultrasonic diagnostic apparatus, comprising:
an ultrasonic probe having ultrasonic transducers configured to transmit and receive ultrasound in a direction of an object to be examined;
a transmission/reception unit configured to drive the ultrasonic transducers to transmit the ultrasound and receive reflected signals from the object;
a data generation unit configured to generate ultrasonic data by processing the received reflected signals obtained by the transmission/reception unit;
an image/time-series data generation unit configured to generate image data and time-series data by processing the ultrasonic data obtained by the data generation unit;
a display mode switching unit configured to input a display mode switching signal for switching a dynamic image display mode and a freeze image display mode;
a display format selection unit configured to allow an operator to select a first display format for the dynamic image display mode and a second display format for the freeze image display mode;
a memory circuit to store the first display format for displaying the image data and the time-series data and the second display format for displaying the image data and the time series data;

a display format setting unit configured to set the first or the second display format by reading stored data of the first or the second display formats from the memory circuit;

a display data generation unit configured to generate display data based on the first display format when the dynamic image display mode is selected corresponding to the display mode switching signal, and to generate display data based on the second display format when the freeze image display mode is selected corresponding to the display mode switching signal; and a display unit configured to display the display data, wherein the first and the second display formats stored in the memory circuit are automatically selected to display the display data in the set format using the display data generation unit according to the display mode switching signal provided from the display mode switching unit.

2. The ultrasonic diagnostic apparatus according to claim 1, further including a region of interest setting unit configured to set a region of interest on the image data, and wherein the image/time-series data generation unit generates the time-series data based on the received signals obtained from an area corresponding to the region of interest set by the region of interest setting unit.

3. The ultrasonic diagnostic apparatus according to claim 1, further including a time-series data measurement unit, and wherein the time-series data measurement unit measures diagnostic parameters by using the time-series data.

4. The ultrasonic diagnostic apparatus according to claim 1, wherein the second display format is set to display the image data and the time-series data by Up/Down.

5. The ultrasonic diagnostic apparatus according to claim 1, further including a display format selection unit for selecting the display format and a selection information storage unit for storing display format selection information, and wherein the display data generation unit generates the display data including at least one of the image data and the time-series data based on the display format corresponding to the newest display format selection information in each of the dynamic image display mode or freeze image display mode stored in the selection information storage unit.

6. The ultrasonic diagnostic apparatus according to claim 1, wherein the image data generated by the image/time-series data generation unit is at least one of B-mode image data and colored Doppler image data.

7. The ultrasonic diagnostic apparatus according to claim 1, wherein the time-series data generated by the image/time-series data generation unit is at least one of M-mode data and Doppler spectrum data.

8. An ultrasonic diagnostic apparatus, comprising:

an ultrasonic probe having ultrasonic transducers configured to transmit and receive ultrasound in a direction of an object to be examined;

a transmission/reception unit configured to drive the ultrasonic transducers to transmit the ultrasound and receive reflected signals from the object;

a data generation unit configured to generate ultrasonic data by processing the received reflected signals obtained by the transmission/reception unit;

an image/time-series data generation unit configured to generate image data and time-series data by processing the ultrasonic data obtained by the data generation unit;

a display mode switching unit configured to input a display mode switching signal for switching a dynamic image display mode and a freeze image display mode;

a display format selection unit configured to allow an operator to select a first display format for the dynamic image display mode and a second display format for the freeze image display mode;

a memory circuit to store the first display format for displaying the image data and the time-series data and the second display format for displaying the image data and the time series data;

a measurement item selection unit configured to select a desired measurement item from a plurality of measurement items for the time-series data;

a display format setting unit configured to set the first or the second display format by reading stored data of the first or the second display format from the memory circuit;

a display data generation unit configured to generate display data based on the first display format when the dynamic image display mode is selected corresponding to the display mode switching signal and to generate display data including the second display format when the freeze image display mode is selected corresponding to the display mode switching signal, the time-series data corresponding to the measurement item selected by the measurement item selection unit; and a display unit configured to display the display data, wherein the first and the second display formats stored in the memory circuit are automatically selected to display the display data in the set format using the display data generation unit according to the display mode switching signal provided from the display mode switching unit.

9. The ultrasonic diagnostic apparatus according to claim 8, further including a region of interest setting unit configured to set a region of interest on the image data, and wherein the image/time-series data generation unit generates the time-series data based on the received signals obtained from an area corresponding to the region of interest set by the region of interest setting unit.

10. The ultrasonic diagnostic apparatus according to claim 8, further including a time-series data measurement unit, and wherein the time-series data measurement unit measures diagnostic parameters by using the time-series data.

11. The ultrasonic diagnostic apparatus according to claim 8, wherein the display format setting unit sets the display format for displaying at least one of the image data and the time-series data based on the measurement item.

12. The ultrasonic diagnostic apparatus according to claim 8, further including a display format selection unit for selecting the display format and a selection information storage unit for storing the display format selection information, and wherein the display data generation unit generates the display data including at least one of the image data and the time-series data based on the display format corresponding to the newest display format selection information in each of the dynamic image display mode or the freeze image display mode stored in the selection information storage unit.

13. The ultrasonic diagnostic apparatus according to claim 8, wherein the image data generated by the image/time-series data generation unit is at least one of B-mode image data and colored Doppler image data.

14. The ultrasonic diagnostic apparatus according to claim 8, wherein the time-series data generated by the image/time-series data generation unit is at least one of M-mode data and Doppler spectrum data.

15. A method of performing ultrasonic measurement, comprising:

selecting, by an operator, a first display format for a dynamic image display mode and a second display format for a freeze image display mode;

storing data of the first display format for displaying image data and time-series data, and storing data of the second display format for displaying image data and time series data;

transmitting ultrasound to an object in a plurality of directions of an object;

receiving signals from the object in response to the transmitted ultrasound;

generating and displaying dynamic image data based on the received signals;

setting a region of interest on the dynamic image data to acquire time-series data;

generating time-series data based on the received signals obtained by receiving ultrasound from an area of the object corresponding to the region of interest, the time-series data being displayed together with the image data under the dynamic image display mode, using the stored data of the first display format;

inputting a display mode switching signal;

changing the dynamic image display mode to the freeze image display mode based on the display mode switching signal to select the second display format by reading the stored data of the second display format automatically according to the changing;

displaying freeze image data and time-series data under the freeze image display mode; and measuring diagnostic parameters based on the display data.

16. The method of ultrasonic measurement according to claim 15, further including the step of:

selecting the display format of the freeze image display mode prior to the step of generating image data.

17. A method of performing ultrasonic measurement, comprising:

selecting, by an operator, a first display format for a dynamic image display mode and a second display format for a freeze image display mode;

storing data of the first display format for displaying image data and time-series data, and storing data of the second display format for displaying image data and time series data;

transmitting ultrasound to an object in a plurality of directions of an object;

receiving signals from the object in response to the transmitted ultrasound;

generating image data based on received signals;

setting a region of interest on a dynamic image to acquire time-series data;

generating time-series data based on the received signals obtained from an area of the object corresponding to the region of interest, the time-series data being displayed together with the image data under the dynamic image display mode using the stored data of the first display format;

inputting a display mode switching signal;

changing the dynamic image display mode to the freeze image display mode based on the display mode switching signal to select the second display format by reading the stored data of the second display format automatically according to the changing;

displaying freeze image data and the time series data under the freeze image display mode using the read data of the second display format;

generating and displaying the image data and the time-series data according to the inputted display mode switching signal;

inputting a selection signal for selecting a measurement item;

setting a display format for measurement mode based on the selection signal;

displaying the display data based on the display format for the measurement mode; and measuring the diagnostic parameter based on the display data.

18. The method of ultrasonic measurement according to claim 17, further including the step of:

selecting the display format corresponding to the measurement item prior to the step of generating the image data.

* * * * *